United States Patent [19]

Zingerman

[11] Patent Number: 4,872,873

[45] Date of Patent: Oct. 10, 1989

[54] CONTROLLED RELEASE BOLUS DEVICE

[75] Inventor: Joel R. Zingerman, Westfield, N.J.

[73] Assignee: Merck & Co., Inc., Rahway, N.J.

[21] Appl. No.: 133,586

[22] Filed: Dec. 14, 1987

[51] Int. Cl.[4] .............................................. A61K 9/22
[52] U.S. Cl. ................................................ 604/892.1
[58] Field of Search ............... 604/890.1, 891.1, 892.1, 604/896, 48, 57

[56] References Cited

U.S. PATENT DOCUMENTS

| | | | |
|---|---|---|---|
| 3,732,865 | 5/1973 | Higuchi et al. | 604/892.1 |
| 4,312,347 | 1/1982 | Magoon et al. | 604/891.1 |
| 4,326,522 | 4/1982 | Guerrero et al. | 604/57 |
| 4,350,271 | 9/1982 | Eckenhoff | 604/892.1 |
| 4,416,659 | 11/1983 | Simpson et al. | 604/57 |
| 4,425,117 | 1/1984 | Hugemann et al. | 604/890.1 |
| 4,479,796 | 10/1984 | Kallok | 604/891.1 |
| 4,624,945 | 11/1986 | Eckenhoff et al. | |
| 4,704,118 | 11/1987 | Eckenhoff | 604/892.1 |

FOREIGN PATENT DOCUMENTS 0164241  12/1985  European Pat. Off. ............ 604/890

Primary Examiner—Max Hindenburg
Assistant Examiner—K. M. Reichle
Attorney, Agent, or Firm—David L. Rose; Hesna J. Pfeiffer; Manfred Polk

[57] ABSTRACT

This invention relates to an improved controlled release bolus device wherein the improvement comprises attaching at the orifice a screen or insert which prevents blockage of the orifice by exogeneous materials, but does not vary the flow of medicament from the device.

3 Claims, 4 Drawing Sheets

FIG. 4
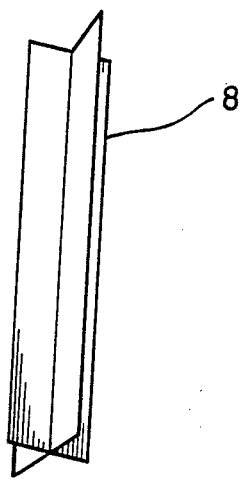
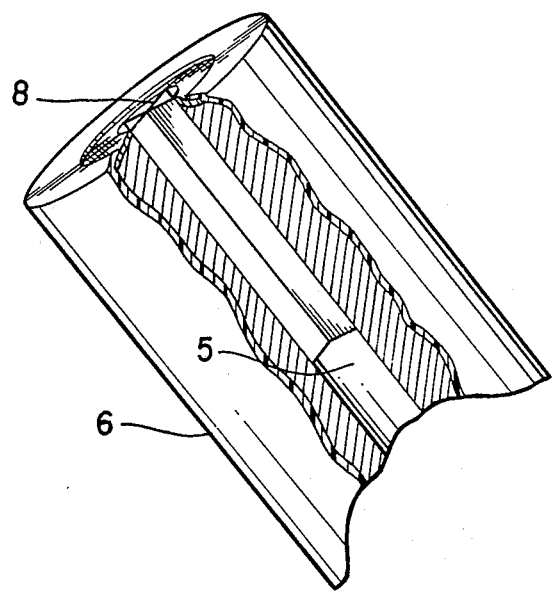
FIG. 5

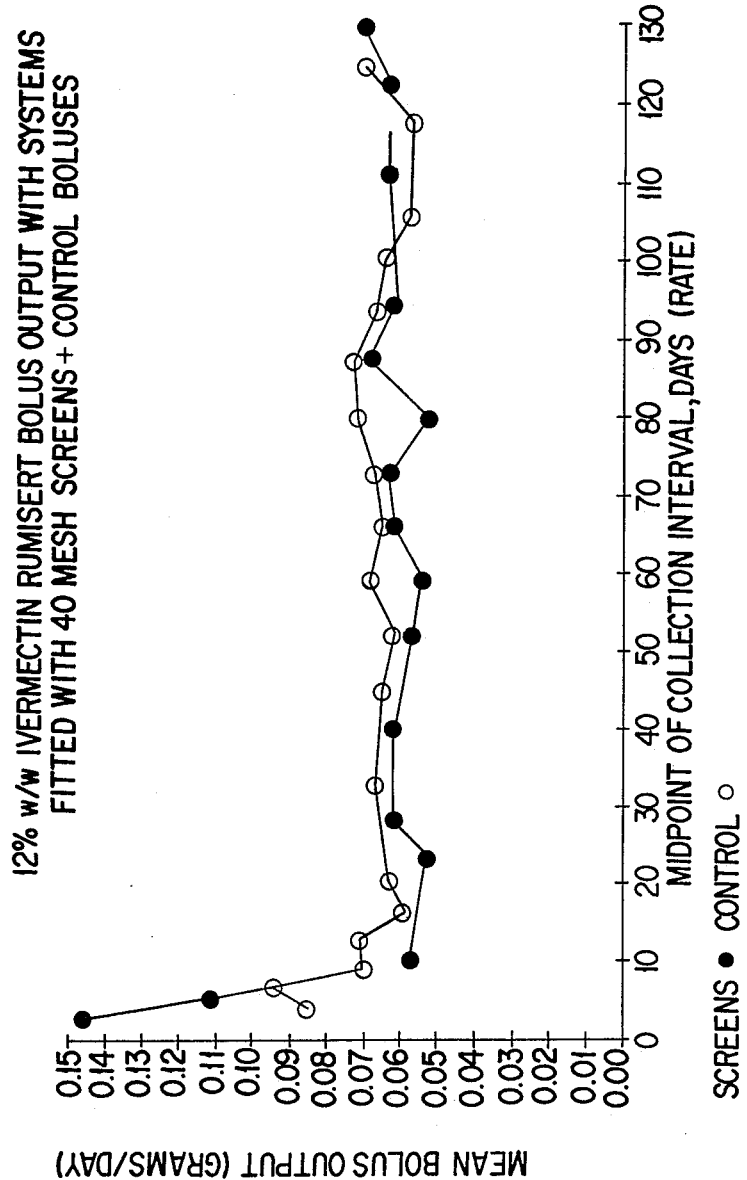

CONTROLLED RELEASE BOLUS DEVICE

BACKGROUND OF THE INVENTION

Throughout the art is disclosed numerous controlled release devices for administering medication such as drugs, as well as food supplements such as vitamins to animals such as livestock (e.g., horses, cattle, pigs, etc.). Heretofore, said medication was primarily administered to animals via feed and syringe methods.

Representative controlled delivery devices disclosed in the art are indicated below:

1. U.S. Pat. No. 4,200,098 (1980)—An osmotic system is disclosed for dispensing a beneficial agent. The system comprises (1) a first wall of a semipermeable material that surrounds a compartment containing a drug formulation, and has a passageway through the wall for releasing agent from the compartment, (2) a second wall positioned distant from the first wall, said second wall a microporous or hydrogel material that extends around the first wall, and (3) a distribution zone interposed between the first and second wall and initially housing a compound soluble in an external fluid that enters the system.

2. U.S. Pat. No. 4,077,407 (1978)—discloses an osmotic device for delivering an active agent. The device is comprised of a wall surrounding a compartment and has a passageway through the wall for releasing the agent. The wall is formed of a multiplicity of materials comprising a material permeable to an external fluid and substantially impermeable to agent and at least one additional material selected from a material that imparts stability to the wall, enhances the permeability of the wall to fluids, or aids in forming the wall. The compartment comprises an active agent that exhibits an osmotic pressure gradient against an external fluid, or the agent is mixed with an osmotically effective compound that exhibits an osmotic pressure gradient against the fluid. Agent is released from the device by fluid being imbibed through the wall into the compartment at a rate controlled by the permeability of the wall and the osmotic pressure gradient across the wall, to produce a solution containing agent that is released through the passageway at a controlled and continuous rate over a prolonged period of time.

3. U.S. Pat. No. 4,160,020 (1979)—An osmotic device is disclosed for delivering an active agent. The device comprises a wall surrounding a compartment with a passageway through the wall for releasing the agent. The wall comprises a material permeable to an external fluid and substantially impermeable to agent and at least one additional material independently selected from materials that impart stability to the wall, enhance the permeability of the wall to fluids, or aid in forming the wall. The compartment contains an agent that exhibits an osmotic pressure gradient across the wall against an external fluid, or the agent is mixed with an osmotically effective compound that exhibits an osmotic pressure gradient against the fluid. Agent is released from the device by fluid being imbibed through the wall into the compartment at a rate controlled by the permeability of the wall and the osmotic pressure gradient across the wall, thereby producing a solution containing agent that is released through the passageway at a controlled rate over time.

4. U.S. Pat. No. 4,327,725 (1982)—An osmotic device is disclosed comprising a semipermeable wall surrounding a compartment housing an agent that is insoluble to very soluble in aqueous and biological fluids, and a layer of a fluid swellable, hydrogel. A passageway in the wall connects the agent with the exterior of the device.

SUMMARY OF THE INVENTION

It has been observed that controlled release bolus devices experience difficulties in maintaining uniform delivery of a beneficial agent in the rumen of animals. The difficulty is caused by foreign matter such as pieces of metal, barbed wire, baling wire, etc. entering the bolus orifice and altering or sometimes completely preventing said beneficial agent from being extruded from the device. Therefore, it is an object of this invention to describe the unexpected results obtained wherein a screen device is inserted into the bolus orifice thereby preventing foreign matter from altering or clogging the orifice and affecting the delivery rate of said beneficial agent from said device.

A further object of the invention is to describe the mechanism wherein the screen does not interfere with the functionability of the bolus, i.e., the beneficial agent is delivered at the normal rate of delivery.

A still further object of the invention is to describe a mechanism which gives rate of delivery of 65-70 mg per day for a 120 day period.

Another object of the invention is to describe the mechanism in which the screen breaks up the solid string of medicament layer, usually in the form of a paste or a melt, such as a wax layer, as it passes through the orifice thereby exposing more surface area, and increasing the rate of utilization of the medicament layer by the animal.

Further objects will become apparent from the description which follows.

DESCRIPTION OF THE INVENTION

It has been found that affixing a screen over the orifice of the controlled delivery bolus devices disclosed herein substantially reduces interference by outside objects with the flow of beneficial agent through the orifice of said devices. The screen device described herein (1) prevents the entrance of foreign matter into the orifice, (2) breaks up the medicament paste or melt being extruded from the orifice and thereby permit faster and more uniform availability of the beneficial agent, and (3) protects the user from contact with the active paste or wax while handling or administering the bolus.

In general, the controlled Release Bolus Device referred to herein is known in the art. Said devices are of various shapes and forms and deliver beneficial substance in various forms such as paste, gels, liquids, etc. Said devices basically comprise an osmotic agent which exerts a pressure against the interface which forces the active agent through the orifice and ultimately the horizontal screen or vertically inserted rigid film sections. The densifier surrounds the orifice and ensures that the device is not regurgitated by the ruminant and all components of the device are surrounded by a membrane excluding said orifice area.

The screen can be positioned horizontally across the orifice or the screen can be in the form of a longitudinal insert within the orifice in the form of a relatively thin, but rigid film extending completely across the orifice with from tow to six radial members. The method of affixing the screen to the orifice is not critical. For example, the screen can be affixed with adhesive agents such as glue or by insertion under the membrane of the device as shown in FIG. 3. The rigid film insert within the orifice would be diametrically arranged in the case of two radial members, and with greater numbers of radial member, all such radial members would meet in a single point in the center of the orifice. The rigid film members would extend for substantially the length of the orifice, but at least half the length to ensure that the insert is not dislodged from the bolus by the force of the exiting material, nor pushed into the device by the force of an outside device such as a piece of wire. The screen or insert positioned in the device can be made of any metal, non-metal or combination thereof having properties suitable for ingestion and capable of being inserted into the orifice of the device and being sufficiently rigid so that it can withstand the forces of any foreign objects attempting to enter the orifice and of the exiting material. However, if made of metal, the screen or insert should be resistant to rusting Generally, the diameter of the orifice is less than 0.200 inch. When employing a horizontal screen, the mesh size ranges from .030 to 0.020 inch (0.85 to 0.5 mm), preferably 0.029 to 0.022 inch (0.73 to 0.56 mm) and most preferably 0.025 inch (0.64 mm) in size (see Figure I). When employing vertical inserts (see Figure II) the number of individual radial arms can range from 2 to 6 and each radial arm would be one-half the diameter of the orifice.

Specifically, a preferred embodiment of the instant improved controlled release bolus can be described as comprising a semipermeable membrane defining a compartment, the compartment being divided into first and second portions by a moveable interface, the first compartment portion containing a swellable agent, the second compartment portion containing a medicament to be dispensed, a densifier within the second compartment adjacent said membrane and a passageway through the membrane and densifier connecting said second compartment portion with the exterior of the bolus, having a central axis and a diameter such that when the bolus is in contact with water, the semipermeable membrane allows water to pass therethrough which is imbibed by the swellable agent which forces the interface to move the medicament to be dispensed through the passageway, wherein the improvement comprises an insert of rigid film having a central axis which is placed coaxially within the passageway, said inset comprising from 2 to 6 arm members connected together at and extending radially from said central axis of said insert a distance of approximately one-half of the diameter of the passageway.

As one skilled in the art can appreciate, the screen or rigid film insert may be used as a release agent for coated materials such as microencapsulated or film coated substances.

The beneficial agents employed in the practice of the invention are not critical. Representative agents are: Anthelmintic, antiparasitic and growth promoting agents such as Avermectin and Milbemycin compounds. Said compounds are known and processes for their preparation are disclosed throughout the art. For example, see U.S. Pat. Nos. 4,310,519 to Albers-Schonberg et al., 4,378,353 to Goegelman et al. and 4,199,569 to Chabala et al. which disclose avermectin compounds and 3,950,360 to Aoki et al. which disclose milbemycin compounds.

Other avermectin derivatives such as monosaccharide and aglycone derivatives are disclosed in U.S. Pat. No. 4,206,205 to Mrozik et al., the acylated derivatives thereof are disclosed in U.S. Pat. No. 4,201,861 to Mrozik et al., the 13-deoxy aglycone compounds are disclosed in Re. 32,034 and Re. 32,006, and the 4″-keto and 4″-amino compounds are disclosed in U.S. Pat. No. 4,427,663 to Mrozik.

The avermectin and milbemycin compounds disclosed therein are useful in treating certain infectious diseases in ruminant animals such as sheep, cattle, goats, horses, swine, and the like.

Also, food supplements such as vitamins and minerals, antibiotics and the like, may be included as the beneficial agent of the bolus.

Some studies which further exemplify the concepts of this invention are shown below.

CONTROLLED RELEASE BOLUS PROTECTIVE SCREEN

To evaluate the feasibility of preventing the entry of wires into the delivery orifice, a "protective screen" concept was tested. Forty-mesh screens (0.025 inch-0.64 mm) were glued on the bolus densifiers (covering the orifice) of three boluses. The output rates of the three systems in 37° C. saline are shown in FIG. 1. After 90° days, the interface exits the bolus The higher viscosity interface exit the screen via a temporary reduced output rate until the osmogen builds up sufficient "power" to effect nominal output of 65–70 mg per day. The average output rate for the three boluses plotted against the "unscreened" controls is shown in FIG. 6. The screens do not appear to have any detrimental effect on the output rate of the active melt compared with the controls. At steady state delivery, there is no difference in the pumping rates of the active agent with and without the screen.

BRIEF DESCRIPTION OF THE DRAWINGS

FIG. 4 shows an enlarged perspective drawing of a rigid film insert having four radial members.

FIG. 5 shows the rigid film having been inserted into the orifice of a bolus shown in a partial perspective view.

In FIGS. 1 and 2, FIG. 1 shows a general configuration of screen 7 for insertion into the top of bolus orifice 5. FIG. 2 shows screen 7 having been affixed over orifice 5. In FIG. 3, which represents an osmotically powered ruminal bolus, there is a drug component 1, which is compressed due to pressure from interface 2 being exerted by an osmotic component 3, that expands due to osmotic inhibition of a liquid, thereby forcing said drug loaded component 1 through orifice 5, which is surrounded by densifier 4, and ultimately through screen 7 inserted into orifice 5. The device is surrounded, except for the orifice by membrane 6. FIG. 4 shows a rigid film four membered component 8 for insertion into orifice 5. FIG. 5 shows said rigid film four radial membered component having been inserted into orifice 5.

Figure 1:
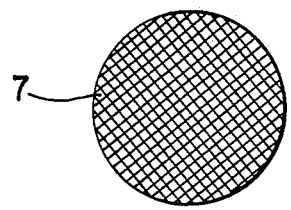
FIG. 1 shows a screen to be affixed horizontally across the top of the densifier over the orifice of bolus. The screen is shown in enlarged view.
Figure 2:
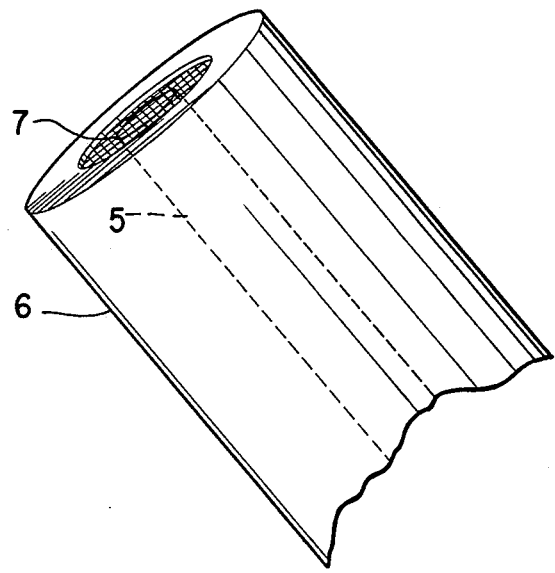
FIG. 2 shows the bolus with a screen placed horizontally across the orifice.
Figure 3:
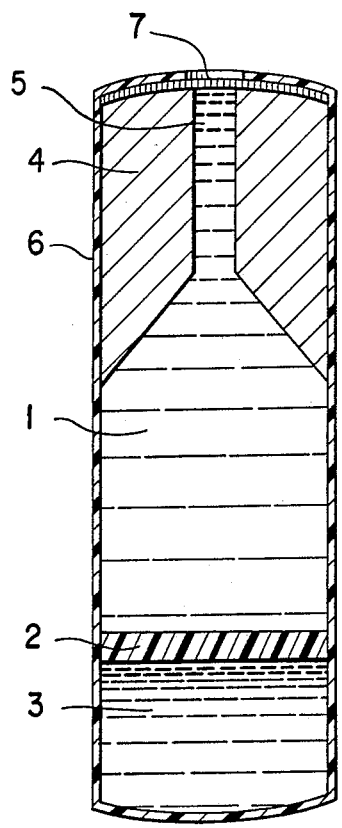
FIG. 3 shows a general configuration of an osmotically powered controlled release device with the screen in place over the orifice of the device.

What is claimed is:

1. An improved controlled release bolus comprising a semipermeable membrane defining a compartment, the compartment being divided into first and second portions by a moveable interface, the first compartment portion containing a swellable agent, the second compartment portion containing a medicament to be dispensed, a densifier within the second compartment adjacent said membrane and a passageway through the membrane and densifier connecting said second compartment portion with the exterior of the bolus, having a central axis and a diameter such that when the bolus is in contact with water, the semipermeable membrane allow water to pass therethrough which is imbibed by the swellable agent which forces the interface to move the medicament to be dispensed through the passageway, wherein the improvement comprises an insert of rigid film having a central axis which is placed coaxially within the passageway, said inset comprising from 2 to 6 arm members connected together at and extending radially form said central axis of said insert a distance of approximately one-half of the diameter of the passageway.

2. The device of claim 1 wherein the rigid film insert extends substantially the length of the passageway.

3. The device of claim 2, wherein the rigid film insert extends at least half the length of the passageway.

* * * * *